United States Patent [19]

Marchetto et al.

[11] Patent Number: 5,082,591
[45] Date of Patent: Jan. 21, 1992

[54] SURFACE ACTIVE AGENT BASED ON POLYOXYALKYLENATED (1-PHENYL ETHYL) PHENOLS, THE PROCESS FOR PREPARATION THEREOF AND THE USE THEREOF FOR PRODUCING EMULSIFIABLE CONCENTRATED SOLUTIONS OF ACTIVE MATERIALS

[75] Inventors: Antonio Marchetto, Saronno; Anghelito Mascheroni, Milan, both of Italy; Georges Ruffo, Vernaison, France

[73] Assignee: Rhone-Poulenc Chimie, Courbevoie Cedex, France

[21] Appl. No.: 357,941

[22] Filed: May 30, 1989

[30] Foreign Application Priority Data

May 27, 1988 [IT] Italy .................. 20777 A/88

[51] Int. Cl.$^5$ .................. B01F 17/42; B01J 13/00; C07C 43/20
[52] U.S. Cl. .................. 252/351; 71/DIG. 1; 252/312; 252/353; 252/DIG. 1; 514/938; 514/939; 514/941; 568/608
[58] Field of Search .................. 252/312, 351, DIG. 1; 514/938, 939, 941; 568/608

[56] References Cited

U.S. PATENT DOCUMENTS

| | | | |
|---|---|---|---|
| 2,903,486 | 9/1959 | Brown et al. | 252/351 X |
| 3,022,335 | 2/1962 | Lundsted | 252/351 X |
| 4,322,312 | 3/1982 | Boehmke | 252/DIG. 1 |
| 4,360,452 | 11/1982 | Zabrocki et al. | 252/DIG. 1 |
| 4,547,199 | 10/1985 | Boehmke et al. | 252/351 X |
| 4,568,480 | 2/1986 | Thir et al. | 252/312 |
| 4,814,000 | 3/1989 | Ciocca et al. | 71/111 X |
| 4,824,663 | 4/1989 | Wirth et al. | 514/938 X |
| 4,828,835 | 5/1989 | Meyers et al. | 514/938 X |

FOREIGN PATENT DOCUMENTS 50-25526 8/1975 Japan.
1057867 2/1967 United Kingdom .................. 514/938

OTHER PUBLICATIONS

*Encyclopedia of Polymer Science and Engineering*, vol. 4, A Wiley–Interscience Publication, John Wiley & Sons, New York (1986), p. 192.

*Primary Examiner*—Richard D. Lovering
*Attorney, Agent, or Firm*—Finnegan, Henderson, Farabow, Garrett, and Dunner

[57] ABSTRACT

A surface active agent formed by a polyoxethylenated and polyoxypropylenated di and/or tri (1-phenyl ethyl) phenol with 16 to 35 statistically distributed recurrent oxyalkylenated units. The ratio between the number of recurrent oxyethylenated units and the number of recurrent oxypropylenated units ranges from 75/25 to 90/10. The surface active agent is prepared by means of the reaction of a di and/or tri (1-phenyl ethyl) phenol and a mixture of monoethylene glycol and monopropylene glycol with a monoethylene giycol/monopropyleneglycol molar ratio ranging from 75/25 to 90/10. The surface active agent can be used for producing concentrated emulsifiable solutions of active materials, in particular phytosanitary materials.

12 Claims, No Drawings

SURFACE ACTIVE AGENT BASED ON POLYOXYALKYLENATED (1-PHENYL ETHYL) PHENOLS, THE PROCESS FOR PREPARATION THEREOF AND THE USE THEREOF FOR PRODUCING EMULSIFIABLE CONCENTRATED SOLUTIONS OF ACTIVE MATERIALS

The present invention concerns a surface active substance based on poly (1-phenyl ethyl) phenols which contain recurrent statistically distributed polyoxyethylenated and polyoxypropylenated units, the process for the preparation thereof and the use thereof for producing emulsifiable concentrated solutions of active materials which are then diluted to obtain emulsions which are ready for use.

It is known that it is possible to prepare biocidal compositions which can be dispersed in water by means of surface active agents of the polyoxyethylenated tri (1-phenyl ethyl) phenol type or which bear recurrent polyoxyethylenated and polyoxypropylenated units which are distributed in accordance with a given sequence (Japanese patent application No. 25526/1975).

A main disadvantage of this type of surface active agent is that the degree of solubility thereof in the organic solvents used in the phytosanitary industry is inadequate.

The inventors have found a surface active agent which is soluble in the organic solvents used in the phytosanitary field.

In accordance with the purpose of the invention as embodied and broadly described herein, there is provided a surface active agent comprising at least one poly-oxyethylenated and -oxypropylenated poly (1-phenyl ethyl) phenol of the following formula (I):

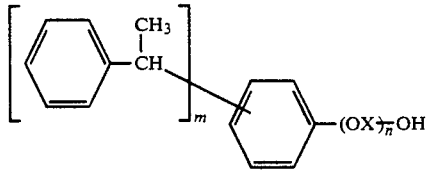

wherein:

m is 2 or 3;

$(OX)_n$ represents a statistical succession of recurrent oxyethylenated units and recurrent oxypropylenated units;

n is such that the total number of recurrent oxyalkylenated units of the radical $(OX)_n$ ranges from approximately 16 to 35, preferably between 20 and 30, with a ratio of recurrent oxyethylenated units to recurrent oxypropylenated units ranging from approximately 75/25 to 90/10, and preferably from 80/20 to 90/10.

The surface agent which is the subject matter of the invention can be prepared by the reaction of at least one poly (1-phenyl ethyl) phenol of formula (II):

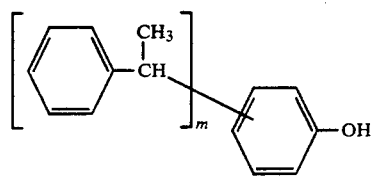

wherein m is 2 or 3 and a mixture of monoethylene glycol and monopropylene glycol with a monoethylene glycol/monopropylene glycol ratio corresponding to the desired ratio between the number of recurrent oxyethylenated units and the number of recurrent oxypropylenated units.

This operation is carried out for a period of time in the range of from 20 to 40 minutes, at a temperature ranging from 140° to 180° C., in the presence of 0.5 to 1.5% by weight with respect to the finished product of an alkaline base, such as soda, as a catalyst. The phenol of formula II together with the monoalkylene glycols equivalent to the product of formula $H-(OX)_n-OH$ are used in stoichiometric or close to stoichiometric amounts.

The present invention also concerns concentrated emulsifiable solutions which are produced by means of the formulation of active materials which are soluble in organic solvents by means of the surface active agent according to the invention.

The following may be mentioned as active materials which can form emulsifiable concentrated solutions: insecticides, acaricides, fungicides and various associations thereof, herbicides, nematocides, molluscicides, substances with an attraction effect, repellent substances, and rodenticides.

As examples of insecticides which are suitable in accordance with the present invention, mention may be made of those which belong to the following families:
organo-halogenated or chlorinated substances;
carbinols;
organo-phosphorated substances;
sulphones and sulphonates;
carbamates;
benzoyl ureas; and
synthetic pyrenthrinoids.

Fungicides which may be used in the present invention may be selected from the following:
carbamates;
derivatives of benzene;
derivatives of phenol;
quinones;
dicarboximides;
amines and amides;
diazines;
sulphamides and sulphur-bearing derivatives;
guanidines;
heterocyclic compounds;
metallic monoethyl phosphites; and
organo-stannic substances.

As chemical substances which have herbicidal properties, mention may be made of those which are included in the following families of chemical products:
Phenolic compounds:
carbamates;
substituted ureas;
diazines;
triazines;
amides;
quaternary ammonium compounds;
benzonitriles;
toluidines; and
triazoles and other substances.

It is preferred that the emulsifiable concentrated solutions comprise:
at least one active material;
an organic solvent of said active material;

a surface active agent according to the present invention optionally comprising the addition of at least one anionic, cationic, non-ionic or amphoteric surface active agents which are usual in this type of use;
a wetting agent;
a stabilizing agent; and
various co-adjuvant substances.

The organic solvents which can be used are those which are normally used in this type of formulation. For example, the aromatic hydrocarbons, cyclohexanone, methylhexahydronaphthalene, tetrahydronaphthalene, dimethylsulphoxide, dimethylformamide, dibutylphthalate, isophorone, N-methylpyrrolidone, and butyrolactone. The solvent may be eliminated if the active material used is a liquid at a temperature of between $-20°$ and $50°$ C.

The surface active agent of the present invention also has wetting capability. Accordingly, the presence of a wetting agent is optional. However, if the presence of such a wetting agent is desired, it is preferably selected from the following:

soaps of alkali metals, such as sodium or potassium salts of $C_8$–$C_{24}$, saturated or unsaturated fatty acids, sodium N-lauryl sarcosinate, and sodium N-acylsarcosinate;

alkaline sulphonates such as alkylsulphonates of the sodium diethylhexylsulphosuccinate type; alkylbenzenesulphonates of the type nonyl- or dodecyl-benzenesulphonates of sodium, di-ethanolamine, triethanolamine or N-methylcyclohexylamine; alkaline alkylnaphthalene sulphonates, and alkaline N-alkyltaurates; and sulphates and sulphur-bearing products such as alkaline alkylsulphates of the sodium laurylsulphate type; polyoxyethylenated and sulphated fatty alcohols; and polyoxyethylenated and sulphated alkylphenols.

Among the optional stabilizing agents, it is preferable to use organic acids selected from halogenated aliphatic monocarboxylic acids (formic, monochloroacetic, propionic, citric and tartric acids, etc.);

hydroxycarboxylic acids which are aliphatic (glycolic, etc.) or aromatic (benzoic, phthalic, etc.), and which are optionally substituted (dichlorobenzoic, dimethoxybenzoic, hydroxybenzoic, dihydroxybenzoic, nitrobenzoic, nitroisophthalic, etc.); and sulphonic acids (methane-sulphonic, benzenesulphonic, p-toluenesulphonic, etc).

The term various co-adjuvant substances defines other ingredients or additives which are usual in the formulation of agricultural products, for example, penetration agents, corrosion inhibitors, and adhesives.

The proportions by weight of the different constituents of the emulsifiable concentrated solutions are preferably as follows:

0.1 to 90 parts by weight of active material;
0.5 to 25 parts by weight of a surface active agent according to the present invention;
0 to 25 parts by weight of wetting agent; and
an amount to make up 100 parts by weight of organic solvent.

The emulsifiable concentrated solutions may be obtained in a known manner, for example, by mixing the different constituents and subjecting them to agitation until homogenized.

Then, the emulsifiable concentrated solutions need only be diluted with an amount of water sufficient to produce emulsions which are ready for use.

The resulting emulsifiable concentrated solutions have the following properties:
good stability with respect to storage, and
good stability once diluted with water at the dosage for use throughout the period of use.

The following examples are given by way of indication and are not to be considered as limiting the scope or spirit of the invention.

EXAMPLE 1

Preparation of the Surface Active Compositions of the Invention

Tristyrylphenol and soda (1% by weight with respect to the finished product) are introduced into a reaction vessel and then monoethylene glycol, and monopropylene glycol are introduced at the same time.

The reaction is performed at 160° C. for 30 minutes.

The relative quantities of monoethylene glycol and monopropylene glycol correspond to the ratios OE/OP set forth in Table I.

The tristyrylphenol and the monoalkylene glycols are used in stoichiometric amounts.

OE represents a recurrent ethylene oxide unit (or ethyoxylated unit) and OP represents a recurrent propylene oxide unit (or propoxylated unit).

EXAMPLES 2 to 8

1 g of surface active agent (SAA) prepared in accordance with Example 1, the characteristics of which are set forth in Table I, is introduced into 20 cm$^3$ of xylene or SHELLSOL which is marketed by SHELL.

The mixture is agitated for 5 minutes, using a magnetic agitator. The appearance of the solution obtained is then observed after a period of 72 hours at 0° C. (CIPAC MT 39.1 method). It is found that all the solutions are clear.

EXAMPLES 9 to 13

The procedures of Examples 2 to 8 are repeated, with the replacement of the surface active agent of the present invention by one of the following products:

Example 9: SOPROPHOR CY/8, ethoxylated tri(1-phenyl ethyl) phenol which has 20 moles of ethylene oxide, and is marketed by RHONE-POULENC.

Example 10: tri(1-phenyl ethyl) phenol, which has a propoxylated $(OP)_{nl}$ sequence and an ethoxylated $(OE)_{n2}$ sequence in a terminal position, that is, a product whose $(OX)_nOH$ group is $(OP)_{nl}(OE)_{n2}OH$, with recurrent OE+OP units equal to 25 and an OE/OP ratio of 90/10.

Example 11: tri(1-phenyl ethyl) phenol, which has an $(OP)_{nl}$ sequence and a $(OE)_{n2}$ sequence in a terminal position, with recurrent OE+OP units equal to 34 and an OE/OP ratio of 90/10;

Example 12: tri (1-phenyl ethyl) phenol, which has a $(OE)_{nl}$ sequence and a $(OP)_{n2}$ sequence in a terminal position, that is, a product in which the $(OX)_nOH$ group is $(OE)_{nl}(OP)_{n2}OH$, with recurrent OE+OP units equal to 25 and an OE/OP ratio of 90/10.

Example 13: tri (1-phenyl ethyl) phenol, which has a $(OE)_{nl}$ sequence and a $(OP)_{n2}$ sequence in a terminal position, with recurrent OE+OP units equal to 34 and an OE/OP ratio of 90/10.

The results of the appearance of the tests appear in Table II (CIPAC MT 39.1 method). None of the resulting solutions were clear and some contained sediments.

COMPARATIVE EXAMPLES 14 to 16

A surface active agent is prepared, the characteristics of which are set forth in Table I, in accordance with the mode of preparation used in Example 1.

Evaluation of the Stability of the Emulsifiable Concentrates

Emulsifiable concentrates having differing active materials were prepared using the following procedure:

Surface active agents (SAA) corresponding to those used in Examples 2-16, were added to four different active materials dissolved in xylene, followed by the addition of calcium dodecylbenzenesulphonate (CaDDBS). The amounts of each constituent used depended upon the active material used:

| | |
|---|---|
| diazinon | 60 parts by weight |
| SAA | 2.6 parts by weight |
| CaDDBS | 2.4 parts by weight |
| xylene | 35 parts by weight |
| lindane | 20 parts by weight |
| SAA | 3.1 parts by weight |
| CaDDBS | 1.9 parts by weight |
| xylene | 75 parts by weight |
| malathion | 50 parts by weight |
| SAA | 3.4 parts by weight |
| CaDDBS | 2.6 parts by weight |
| xylene | 45 parts by weight |
| trifluralin | 25 parts by weight |
| SAA | 2.3 parts by weight |
| CaDDBS | 2.7 parts by weight |
| xylene | 70 parts by weight |

The mixtures obtained were subjected to agitation until homogenized resulting in emulsifiable concentrated liquid compositions.

The stability of the resulting emulsions is measured using the CIPAC MT 36.1 method in standardized waters A (20 ppm hardness), D (342 ppm hardness) and C (500 ppm hardness) after 60 or 120 minutes.

The results of the stability test are set forth in Tables III and IV.

It was found that it is impossible to prepare emulsifiable concentrates using the products of Examples 14 to 16.

TABLE I

| EXAMPLE | OE + OP | OE/OP | APPEARANCE OF THE SOLUTION Pure SAA in | |
|---|---|---|---|---|
| | | | xylene | SHELLSOL |
| 2 | 16 | 90/10 | clear | clear |
| 3 | 20 | 90/10 | " | " |
| 4 | 25 | 90/10 | " | " |
| 5 | 34 | 90/10 | " | " |
| 6 | 25 | 84/16 | " | " |
| 7 | 20 | 80/20 | " | " |
| 8 | 25 | 80/20 | " | " |
| 14 | 16 | 50/50 | " | " |
| 15 | 25 | 50/50 | " | " |
| 16 | 34 | 50/50 | " | " |

TABLE II

| EX-AMPLE | OE + OP | OE/OP | APPEARANCE OF THE SOLUTION Pure SAA in | |
|---|---|---|---|---|
| | | | xylene | SHELLSOL |
| 9 | 20 OE | 100/0 | 0.5%* | 0.5%* |
| 10 | 25 − OP + OE | 90/10 | 5%* | 15%* |
| 11 | 34 − OP + OE | 90/10 | 2%* | 48%* |
| 12 | 25 − OE + OP | 90/10 | cloudy | 5%* |
| 13 | 34 − OE + OP | 90/10 | cloudy | 35%* |

*amounts of sedimented substances

TABLE III

| ACTIVE MATERIAL | | DIAZINON | | | LINDANE | | | MALATHION | | | TRIFLURALIN | | |
|---|---|---|---|---|---|---|---|---|---|---|---|---|---|
| Product of Example | Time after dilution | Stability of the emulsion - cream in ml - | | | | | | | | | | | |
| | | A | D | C | A | D | C | A | D | C | A | D | C |
| 2 | 60 | 0 | 0 | 0 | 0 | 0 | 0 | 0 | 0.1 | 0.2 | 0.5 | 0 | 0 |
| | 120 | 0.5 | 0 | 0 | 0 | 0 | 0 | 2.5 | 1 | 0.5 | 2 | 0 | 0 |
| 3 | 60 | 1 | 0 | 0 | 0 | 0 | 0 | 0.6 | 0 | 0 | 0.5 | 0 | 0 |
| | 120 | 2 | 0 | 0 | 0 | 0 | 0 | 1 | 0 | 0 | 1 | 0 | 0 |
| 4 | 60 | 0 | 0 | 0 | 0 | 0 | 0 | 0 | 0 | 0 | 1.5 | 0 | 0 |
| | 120 | 0.5 | 0 | 0 | 0 | 0 | 0 | 0.7 | 0 | 0 | 2 | 0.05 | 0.05 |
| 5 | 60 | 0 | 0 | 0 | 0 | 0 | 0 | 0 | 0 | 0 | 2 | 0.5 | 0.05 |
| | 120 | 0.5 | 0 | 0 | 0 | 0 | 0 | 1.2 | 0.1 | 0.05 | 2.5 | 1 | 1 |
| 6 | 60 | 0.2 | 0 | 0 | 0 | 0 | 0 | 0.5 | 0 | 0 | 0 | 0 | 0 |
| | 120 | 0.5 | 0 | 0 | 0.5 | 0 | 0 | 1 | 0 | 0 | 1 | 0 | 0.5 |
| 7 | 60 | — | — | — | 0 | 0 | 0 | 0.6 | 0 | 0 | 1 | 0 | 0 |
| | 120 | — | — | — | 0 | 0 | 0 | 1.1 | 0 | 0 | 2 | 0 | 0 |
| 8 | 60 | 0 | 0 | 0 | 0 | 0 | 0 | 0.4 | 0 | 0 | 0 | 0 | 0 |
| | 120 | 0.5 | 0 | 0 | 0 | 0 | 0 | 0.8 | 0 | 0 | 0.5 | 0 | 1 |

TABLE IV

| ACTIVE MATERIAL | | DIAZINON | | | LINDANE | | | MALATHION | | | TRIFLURALIN | | |
|---|---|---|---|---|---|---|---|---|---|---|---|---|---|
| Product of Example | Time after dilution | Stability of the emulsion - cream in ml - | | | | | | | | | | | |
| | | A | D | C | A | D | C | A | D | C | A | D | C |
| 9 | 60 | 0.2 | 0 | 0 | 0 | 0 | 0 | 0.4 | 0 | 0 | 0.5 | 0 | 0 |
| | 120 | 0.5 | 0 | 0 | 0 | 0 | 0 | 0.8 | 0 | 0 | 1.5 | 0.1 | 0 |
| 10 | 60 | 1 | 0 | 0 | 0 | 0 | 0 | 0.4 | 0 | 0 | 0.5 | 0 | 0 |
| | 120 | 2 | 0 | 0 | 0 | 0 | 0 | 0.8 | 0 | 0 | 1.5 | 0.1 | 0 |
| 11 | 60 | 1 | 0 | 0 | 0 | 0 | 0 | 1 | 0 | 2 | 0.5 | 0 | 0 |
| | 120 | 2 | 0 | 0 | 0.5 | 0 | 0.5 | 2 | 0.1 | 5 | 1.5 | 0 | 1.2 |
| 12 | 60 | 1 | 0 | 0 | 0 | 0 | 0 | 0 | 0.05 | 5 | 2 | 0.5 | 0.5 |
| | 120 | 2 | 0 | 0.2 | 0.5 | 0.5 | 0.5 | 0.1 | 5 | 6 | 3 | 1 | 1 |
| 13 | 60 | 1 | 0 | 0 | 0 | 0 | 0 | 2 | 0.6 | 0.3 | 1.5 | 0.5 | 5 |
| | 120 | 2 | 0 | 0.5 | 0 | 0 | 0 | 3.5 | 1.2 | 0.7 | 2 | 1 | 6 |
| 14 | 60 | negative | | | negative | | | negative | | | negative | | |
| | 120 | | | | | | | | | | | | |

TABLE IV-continued

| ACTIVE MATERIAL | | DIAZINON | | | LINDANE | | | MALATHION | | | TRIFLURALIN | | |
|---|---|---|---|---|---|---|---|---|---|---|---|---|---|
| Product of Example | Time after dilution | Stability of the emulsion - cream in ml - | | | | | | | | | | | |
| | | A | D | C | A | D | C | A | D | C | A | D | C |
| 15 | 60 | negative | | | negative | | | negative | | | negative | | |
| | 120 | | | | | | | | | | | | |
| 16 | 60 | negative | | | negative | | | negative | | | negative | | |
| | 120 | | | | | | | | | | | | |

Additional advantages and modifications will readily occur to those skilled in the art. The invention in its broader aspects is, therefore, not limited to the specific details, representative apparatus and illustrative examples shown and described. Accordingly, departures may be made from such details without departing from the spirit and scope of the general inventive concept as defined by the appended claims and their equivalents.

What is claimed is:

1. A surface active agent comprising at least one polyoxyethylenated and -oxypropylenated poly (1-phenyl ethyl) phenol of formula (I)

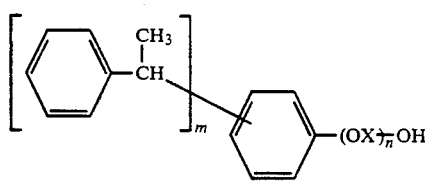

wherein:
m is 2 or 3;
$(OX)_n$ represents a statistical succession of recurrent oxyethylenated units and recurrent oxypropylenated units which are not distributed in accordance with a block sequence;
n being such that the total number of recurrent oxyalkylenated units of the radical $(OX)_n$ ranges from approximately 16 to 35, and wherein the ratio of recurrent oxyethylenated units and oxypropylenated units ranges from approximately 75/25 to 90/10.

2. The surface active agent of claim 1, wherein the ratio between the number of recurrent oxyethylenated units and the number of recurrent oxypropylenated units ranges from approximately 30/20 to 90/10.

3. A process for the preparation of the surface active agent. of claim 1, comprising the step of reacting at least one poly (1-phenyl ethyl ) phenol of formula (II):

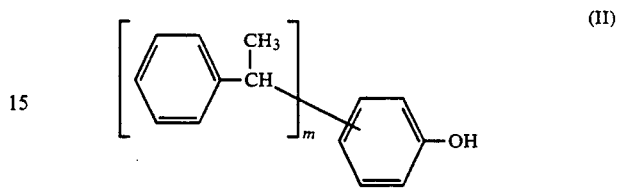

wherein
m is 2 or 3
with a mixture of monoethylene glycol and monopropylene glycol in a molar ratio corresponding to the desired ratio between the number of recurrent oxyethylenated units and oxypropylenated units, and where the molar ratio between the phenol of formula II and monoalkylene glycols are equivalent to a product of formula $H—(OX)_n—OH$ in stoichiometic or close to stoichiometric amounts.

4. The process of claim 3, wherein the molar ratio between monoethylene glycol and monopropylene glycol ranges from approximately 75/20 to 90/10.

5. The process of claim 4, wherein the reaction is carried out at a temperature in the range of 140° to 180° C. in the presence of an alkaline base as a catalyst.

6. The process of claim 4, wherein the molar ratio between monoethylene glycol and monopropylene glycol ranges from approximately 80/20 and 90/10.

7. The process of claim 6, wherein the reaction is carried out at a temperature in the range of 140° to 180° C. in the presence of an alkaline base as a catalyst.

8. The process of claim 3, wherein the reaction is carried out at a temperature in the range of 140° to 180° C. in the presence of an alkaline base as a catalyst.

9. The process of claim 8, wherein said alkaline base is used in an amount of 0.5 to 1.5% by weight with respect to the finished product.

10. An emulsifiable concentrated solution of a phytosanitary active material comprising an emulsifiable active material and the surface active agent of claim 1.

11. An emulsifiable concentrated solution of a phytosanitary active material comprising an emulsifiable active material and the surface active agent of claim 2.

12. An emulsifiable concentrated solution of a phytosanitary active material comprising:
 0.1 to 90 parts by weight of emulsifiable active material;
 0.5 to 25 parts by weight of a surface active agent of claim 1;
 0 to 25 parts by weight of a wetting agent; and
 an amount to make up 100 parts by weight of an organic solvent.

* * * * *

UNITED STATES PATENT AND TRADEMARK OFFICE
CERTIFICATE OF CORRECTION

PATENT NO. : 5,082,591
DATED : January 21, 1992
INVENTOR(S) : Antonio Marchetto et al.

It is certified that error appears in the above-identified patent and that said Letters Patent is hereby corrected as shown below:

Abstract, line 1, change "polyoxethylenated" to --polyoxyethylenated--.

Abstract, line 10, change "giycol" to --glycol--.

Claim 2, column 7, line 62, change "30/20" to --80/20--.

Claim 3, column 7, line 64, after "agent" delete ".".

Claim 3, column 8, line 28, change "stoichiometic" to --stoichiometric--.

Signed and Sealed this

Third Day of August, 1993

Attest:

MICHAEL K. KIRK

*Attesting Officer*  *Acting Commissioner of Patents and Trademarks*